(12) United States Patent
Kouno et al.

(10) Patent No.: US 8,378,152 B2
(45) Date of Patent: *Feb. 19, 2013

(54) METHOD OF PRODUCING PROPYLENE GLYCOL

(75) Inventors: Hiroshi Kouno, Ichihara (JP); Shuji Ozawa, Yokohama (JP); Naritoshi Yoshimura, Funabashi (JP)

(73) Assignee: Mitsui Chemicals, Inc., Tokyo (JP)

( * ) Notice: Subject to any disclaimer, the term of this patent is extended or adjusted under 35 U.S.C. 154(b) by 51 days.

This patent is subject to a terminal disclaimer.

(21) Appl. No.: 12/989,892

(22) PCT Filed: Apr. 21, 2009

(86) PCT No.: PCT/JP2009/057888
§ 371 (c)(1),
(2), (4) Date: Oct. 27, 2010

(87) PCT Pub. No.: WO2009/133787
PCT Pub. Date: Nov. 5, 2009

(65) Prior Publication Data
US 2011/0040131 A1    Feb. 17, 2011

(30) Foreign Application Priority Data

Apr. 30, 2008  (JP) .................. 2008-119026
Jun. 13, 2008  (JP) .................. 2008-155666

(51) Int. Cl.
*C07C 27/00*    (2006.01)
(52) U.S. Cl. ...................................... 568/861
(58) Field of Classification Search ........................ None
See application file for complete search history.

(56) References Cited

U.S. PATENT DOCUMENTS

| | | | | |
|---|---|---|---|---|
| 4,199,479 A * | 4/1980 | Wilkes | ........................ | 502/174 |
| 4,283,581 A | 8/1981 | Wilkes | | |
| 5,214,219 A * | 5/1993 | Casale et al. | .................. | 568/861 |
| 8,053,608 B2 * | 11/2011 | Kouno et al. | ................ | 568/861 |
| 2007/0149830 A1 | 6/2007 | Tuck et al. | | |
| 2010/0036175 A1 | 2/2010 | Franke et al. | | |
| 2010/0256425 A1 | 10/2010 | Kouno et al. | | |

FOREIGN PATENT DOCUMENTS

| | | |
|---|---|---|
| DE | 4302464 | 8/1994 |
| EP | 0523015 | 1/1993 |
| JP | 57-122941 | 7/1982 |
| WO | 2008/049470 | 5/2008 |

OTHER PUBLICATIONS

Extended European Search Report issued on Oct. 19, 2011 for corresponding application No. 09738724.5.
Shauai Wang and Haichao Liu, Selective hydrogenolysis of glycerol to propylene glycol on Cu-ZnO catalysts, Catalysis Letters, vol. 117, p. 62-67, 2007.
International Search Report for PCT/JP2008/069527 mailed Dec. 2, 2008.
Park, et al., Applied Catalysis A: General, 2003, vol. 253, pp. 249-255.
U.S. Office Action, from related U.S. Appl. No. 12/740,197 dated Feb. 24, 2011.
Specification, Claims and Abstract of related U.S. Appl. No. 12/740,197, filed Apr. 28, 2010 (now U.S. Patent No. 8053608, issued Nov. 8, 2011).

* cited by examiner

*Primary Examiner* — Sudhakar Katakam

(74) *Attorney, Agent, or Firm* — Rankin, Hill & Clark LLP

(57) ABSTRACT

Propylene glycol is produced by a method of producing propylene glycol, the method including: obtaining propylene glycol by performing catalytic hydrogenation of glycerol in the presence of a catalyst, the catalyst containing zinc oxide and at least one of copper and copper oxide, and the catalyst, after being reduced at 180° C. to 230° C. in the presence of hydrogen, showing a half width of from 0.4 to 1.1 of a peak having a peak top at a position at which a diffraction angle (2θ±0.2°) is 43.1° in an X-ray diffraction pattern obtained using CuKα as a radiation source.

17 Claims, No Drawings

METHOD OF PRODUCING PROPYLENE GLYCOL

TECHNICAL FIELD

The present invention relates to a method of producing propylene glycol using glycerol as a raw material.

BACKGROUND ART

In recent years, fuels for use in a diesel engine called biodiesel, which are produced from plant and/or animal fat and oil as raw materials, have been developed as part of countermeasures for suppressing global warming. In the process of producing the biodiesel, glycerol is produced as a side product in an amount of about 10% with respect to the oil as a raw material, and the effective use of the glycerol has been intensively studied.

On the other hand, propylene glycol, which is a compound in which a hydroxy group at the 1-position of the glycerol is converted to hydrogen, has been widely used in the fields of pharmaceuticals, cosmetics, foods and the like as a moisturizer, a lubricant, an emulsifier, an anti-freezing liquid, a solvent or the like, since this compound is less toxic to organisms as well as tasteless and odorless. In general, propylene glycol is produced by oxidizing propylene derived from petroleum called a fossil raw material to give propylene oxide, and then hydrating the same.

Regarding the effective use of glycerol, a method of converting glycerol to propylene glycol using a copper catalyst is known. Specifically, a method is disclosed in which glycerol is converted to propylene glycol and ethylene glycol by allowing the glycerol to react with hydrogen in the presence of a catalyst containing copper oxide and zinc oxide (see, for example, Patent Document 1).

The above disclosure merely discloses catalysts whose atomic ratio of copper to zinc (copper/zinc) is from 0.2 to 6, and details such as the conditions for producing the catalyst are not disclosed. In addition, due to the low catalytic activity, the yield of propylene glycol per unit volume and unit time of the catalyst-filled layer (hereinafter sometimes referred to as "space time yield") is insufficient.

Further, a method is disclosed in which glycerol is converted to propylene glycol by allowing the glycerol to react with hydrogen in the presence of a catalyst containing copper and zinc (see, for example, Patent Document 2). However, details of the catalyst are not described.

Moreover, a method is disclosed in which glycerol is converted to propylene glycol by allowing the glycerol to react with hydrogen in the presence of a catalyst, which catalyst is obtained by allowing copper nitrate and zinc nitrate to react with urea, drying the reactant at 110° C. for 3 hours, and then calcining the same at a temperature of 300° C. for 3 hours (see, for example, Non-Patent Document 1).

Patent Document 1: U.S. Pat. No. 5,214,219
Patent Document 2: DE Patent Application Laid-Open Publication No. 4302464
Non-Patent Document 1: Catalysis Letters, Vol. 117, p. 62, 2007

DISCLOSURE OF THE INVENTION

Means for Solving the Problem

It is an object of the present invention to provide a method of producing propylene glycol from glycerol as a raw material, the method achieving a high catalytic activity and a high yield of propylene glycol per unit volume and unit time of the catalyst-filled layer.

Technical Solution

The present inventors have made extensive studies focusing on the fact that the peak of copper and the peak of zinc oxide shown in X-ray diffraction measurement of a catalyst containing zinc oxide and at least one of copper and copper oxide, which is used for the production of propylene glycol from glycerol as a raw material, are separated from each other. As a result, the present inventors have found that the above problem can be solved by using a catalyst containing zinc oxide and at least one of copper and copper oxide from which a specific X-ray diffraction spectrum is obtained, thereby leading to the completion of the present invention.

Specifically, the first embodiment of the present invention is directed to a method of producing propylene glycol, the method comprising:

obtaining propylene glycol by performing catalytic hydrogenation of glycerol in the presence of a catalyst, the catalyst comprising a first component containing at least one of copper and copper oxide and a second component containing zinc oxide, and the catalyst, after being reduced at 180° C. to 230° C. in the presence of hydrogen, showing a half width of from 0.4 to 1.1 of a peak having a peak top at a position at which a diffraction angle $(2\theta\pm0.2°)$ is 43.1° in an X-ray diffraction pattern obtained using $CuK\alpha$ as a radiation source.

The catalyst preferably satisfies a weight ratio of the first component to the second component ((total weight of copper and copper oxide)/(weight of zinc oxide)) to be in a range of from 30/70 to 70/30, and more preferably in a range of from 40/60 to 60/40.

It is also preferable that the catalyst further contains a third component other than copper, copper oxide or zinc oxide, more preferably containing the third component in an amount of 25% by weight or less, and even more preferably containing at least one selected from silica, iron oxide and magnesium oxide as the third component.

It is also preferable that the catalyst be subjected to a calcination treatment at a calcination temperature of from 400° C. to 500° C. for a calcination time of from 2.5 hours to 6 hours.

It is also preferable that the catalytic hydrogenation of glycerol be carried out at a reaction pressure of from 2 to 30 MPa and a reaction temperature of from 150 to 250° C., more preferably at a reaction pressure of from 2 to 30 MPa and a reaction temperature of from 180 to 220° C.

Effects of the Invention

The present invention can provide a method of producing propylene glycol from glycerol as a raw material, the method achieving a high catalytic activity and a high yield of propylene glycol per unit volume and unit time of the catalyst-filled layer (hereinafter sometimes referred to as "space time yield"). As a result, the present invention can produce propylene glycol at a high conversion and a high selectivity, as well as a high space time yield, thereby producing propylene glycol efficiently in industrial production. In addition, the size of facilities can be minimized and the purification load after the reaction can be reduced.

BEST MODE FOR CARRYING OUT THE INVENTION

Hereinbelow, the present invention will be described in detail.

The method of producing propylene glycol of the present invention includes a step of obtaining propylene glycol by performing catalytic hydrogenation of glycerol in the presence of a catalyst, the catalyst including a first component containing at least one of copper and copper oxide and a second component containing zinc oxide, and the catalyst after being reduced at 180° C. to 230° C. in the presence of hydrogen showing a half width of from 0.4 to 1.1 of a peak having a peak top at a position at which a diffraction angle (2θ±0.2°) is 43.1° in an X-ray diffraction pattern obtained by using CuKα as a radiation source.

The catalyst used in the present invention contains the first component containing at least one of copper and copper oxide and the second component containing zinc oxide, and after being reduced at 180° C. to 230° C. in the presence of hydrogen, shows a half width ranging from 0.4 to 1.1 of a peak having a peak top at a position at which a diffraction angle (2θ±0.2° is 43.1° in an X-ray diffraction pattern obtained by using CuKα as a radiation source. This catalyst is referred to as a "specific catalyst" in the following description.

Generally, when a catalyst including a first component containing at least one of copper and copper oxide and a second component containing zinc oxide is reduced in the presence of hydrogen, copper oxide is reduced to copper. Thus, the specific catalyst may contain either one of copper or copper oxide, or may contain copper and copper oxide at an arbitrary ratio. The specific catalyst is not specifically limited as long as it contains zinc oxide and at least one of copper and copper oxide, and after being reduced under the above-described conditions, shows a half width ranging from 0.4 to 1.1 of a peak having a peak top at a position at which a diffraction angle (2θ±0.2°) is 43.1° in an X-ray diffraction pattern obtained by using CuKα as a radiation source.

The weight ratio of the at least one of copper and copper oxide to the zinc oxide ((total weight of copper and copper oxide)/(weight of zinc oxide)) in the specific catalyst is preferably from 30/70 to 70/30, more preferably from 40/60 to 70/30, and even more preferably from 40/60 to 60/40, in view of achieving a high conversion of glycerol.

Further, the specific catalyst may further contain at least one kind of a third component, in addition to copper, copper oxide and zinc oxide, as long as the effect of the present invention is not impaired.

The third component is not particularly limited as long as it is not copper, copper oxide or zinc oxide, and it may be a metal oxide or a metal itself. Examples of the metals that may be included in the third component include metals of Group IIa such as magnesium, barium and the like, metals of Group En such as aluminum and the like, metals of Group IVa such as zirconium and like, metals of Group IVb such as silicon and the like, metals of Group VIa such as chromium and the like, metals of Group VIIa such as manganese, iron and the like, and metals of Group VIII such as cobalt, nickel, and the like. Among them, at least one selected from magnesium, silicon and iron is preferable. Further, the third component is preferably at least one selected from magnesium oxide, iron oxide and silica, from the viewpoint of the conversion of glycerol.

The third component may be contained singly or as a mixture of two or more kinds thereof in the specific catalyst.

The content of the third component in the specific catalyst is preferably 25% by weight or less, and more preferably 20% by weight or less, from the viewpoint of a high conversion of glycerol. Further, the third component is preferably contained in the specific catalyst by substituting part of zinc oxide in the specific catalyst. Specifically, the weight ratio of the at least one of copper and copper oxide to the zinc oxide and the third component ((total weight of copper and copper oxide)/(total weight of zinc oxide and the third component)) is preferably from 30/70 to 70/30, and more preferably from 40/60 to 60/40, from the viewpoint of achieving a high conversion of glycerol.

The content of copper, copper oxide, zinc oxide and the third component in the specific catalyst can be measured by wavelength dispersive X-ray fluorescence analysis (for example, device: XRF-1700, manufactured by Shimadzu Corporation, X-ray tube: Rh, 40 kV, 95 mA, Aperture: φ3 mm, measurement atmosphere: vacuum, analysis method: fundamental parameter method).

The specific catalyst is a catalyst which shows, after being reduced at 180° C. to 230° C. in the presence of hydrogen before the production of propylene glycol, a half width ranging from 0.4 to 1.1 of a peak having a peak top at a position at which a diffraction angle (2θ±0.2°) is 43.1° in an X-ray diffraction pattern obtained by using CuKα as a radiation source. Generally, when propylene glycol is produced by performing catalytic hydrogenation of glycerol using a catalyst containing zinc oxide and at least one of copper and copper oxide, the half width shifts from a higher value to a lower value during the reaction. The half width as mentioned herein is directed to that of a catalyst before the production of propylene glycol.

The half width of a peak having a peak top at a position at which a diffraction angle (2θ±0.2°) is 43.1° in an X-ray diffraction pattern obtained by using CuKα as a radiation source is determined through the following steps (i) and (ii):

(i) a step of reducing a catalyst containing zinc oxide and at least one of copper and copper oxide at 180° C. to 230° C. in the presence of hydrogen to reduce copper oxide to copper; and (ii) a step of measuring the half width of a peak having a peak top at a position at which a diffraction angle (2θ±0.2°) is 43.1° in an X-ray diffraction pattern, by measuring an X-ray diffraction of the catalyst in which the copper oxide has been reduced to copper.

In the present invention, a specific catalyst obtained by the steps above and shows a half width of the obtained peak being in a range of from 0.4 to 1.1 is used.

Next, steps (i) and (ii) will be described in detail.

(i) Step of reducing a catalyst containing zinc oxide and at least one of copper and copper oxide at 180° C. to 230° C. in the presence of hydrogen to reduce copper oxide to copper (hereinafter referred to as "step (i)").

In step (i), a copper/zinc oxide catalyst is obtained by performing catalytic reduction of a catalyst containing zinc oxide and at least one of copper and copper oxide with hydrogen. The temperature at which reduction of the catalyst is initiated varies depending on the copper/zinc ratio and the content of the third component, but in the present invention, reduction of the catalyst is carried out at a temperature in a range of from 180° C. to 230° C. In the present invention, if the specific catalyst does not include the third component, reduction of the catalyst is preferably carried out at a temperature in a range of from 185° C. to 210° C., and more preferably at a temperature in a range of from 185° C. to 200° C. Further, if the specific catalyst includes a third component, reduction of the catalyst is preferably carried out at a temperature in a range of from 200° C. to 230° C., and more preferably at a temperature in a range of from 210° C. to 225° C.

The reduction may be carried out over 2 hours.

Step (i) will be specifically described.

In step (i), specifically, 0.75 g to 1.0 g of a catalyst as a sample are charged in a glass reaction tube capable of measuring an inside temperature (a temperature of the inside of the catalyst layer, measured by a thermocouple located in the middle of the height of the catalyst layer in a glass reaction tube) and an outside temperature (a temperature of the outside of the reaction tube, measured by a thermocouple located on the outer wall of a glass reaction tube in the middle of the height of the catalyst layer). The glass reaction tube is appropriately selected and used such that the height of the catalyst layer is from 0.4 to 2.0 cm. In this way, the catalyst is reduced by allowing the same to contact hydrogen at an inside temperature of from 180° C. to 200° C. Since the reduction reaction is an exothermic reaction, both the inside and outside temperatures are elevated. The temperature is controlled so that the higher one of the inside and outside temperatures does not exceed 230° C. Using hydrogen in an amount with which the reduction can complete within two hours by diluting the same with a nitrogen gas makes it easier to control the temperature. The reduced catalyst thus obtained (copper/zinc oxide-containing catalyst) is recovered under a nitrogen atmosphere.

In the present invention, when the specific catalyst does not include the third component, it is preferable to reduce the catalyst by contacting the same to hydrogen at an inside temperature of 180° C. and control the temperature such that the higher one of the inside temperature or the outside temperature does not exceed 230° C., more preferably does not exceed 210° C., and even more preferably does not exceed 200° C.

When the specific catalyst includes the third component, it is preferable to reduce the catalyst by contacting the same to hydrogen at an inside temperature of 200° C. and control the temperature such that the higher one of the inside temperature or the outside temperature does not exceed 230° C., more preferably does not exceed 210° C.

(ii) Step of measuring the half width of a peak having a peak top at a position at which a diffraction angle ($2\theta \pm 0.2°$) is 43.1° in an X-ray diffraction pattern by measuring an X-ray diffraction of the catalyst in which the copper oxide has been reduced to copper Step (ii) includes the following substeps (ii-1) and (ii-2).

(ii-1) preparing a sample for X-ray diffraction measurement of a copper/zinc oxide-containing catalyst A sample for X-ray diffraction measurement is prepared by sealing the copper/zinc oxide-containing catalyst that has been reduced in step (i) in a resin. The resin used in this step is a clear lacquer that does not contain a pigment, which is a nitrocellulose resin generally used for finishing of interior wood portions or wood products so that a woodgrain pattern of the product can be seen. One example of such a clear lacquer is CLEAR LACQUER (trade name), manufactured by Washin Paint Co., Ltd.

When the reduced copper/zinc oxide-containing catalyst is sealed in the resin, the catalyst is used in an amount of 0.35 g to 0.4 g. Specifically, 0.35 g to 0.4 g of the catalyst are weighed and transferred to an agate mortar in a nitrogen box, and 0.2 ml to 0.4 ml of acetone are added to wet the catalyst. Then, 3.5 ml to 4 ml of the lacquer thinner is added and the mixture is stirred in order to evaporate the solvent. Although it depends on the atmospheric temperature, a viscous liquid suspension is obtained after 20 minutes to 40 minutes. This suspension is applied on a glass cell for X-ray diffraction, and dried at room temperature overnight to form a thin film. These operations are carried out under a nitrogen atmosphere.

(ii-2) measuring the X-Ray diffraction and the half width of the copper/zinc oxide-containing catalyst Next, the X-ray diffraction of the copper/zinc oxide-containing catalyst obtained is measured. The X-ray diffraction of the sample for X-ray measurement prepared in a nitrogen atmosphere is measured under an air atmosphere using Cu and K$\alpha$1 as radiation sources, and the measurement is carried out within 8 hours after placing the sample for X-ray measurement in air.

As a result of performing the X-ray diffraction measurement of the copper/zinc oxide-containing catalyst, peaks having a peak top at a position at which a diffraction angle ($2\theta \pm 0.2°$) is 31.5°, 34.0°, 36.0°, 43.1°, 56.4°, 62.7° or 67.7° are obtained. In the present invention, a peak having a peak top at 43.1° is used.

The half width as mentioned herein refers to a width of a peak at a position corresponding to ½ of the height of the peak obtained by X-ray diffraction measurement. In the present invention, the half width of a peak having a peak top at 43.1° (hereinafter sometimes simply referred to as "half width") is measured. The half width can be typically calculated by using a commercially available software after measuring the X-ray diffraction. Exemplary softwares include "RINT 2000 series application software, Analysis of Crystallite Size and Lattice Strain", manufactured by Rigaku Corporation.

Among various kinds of catalysts containing zinc oxide and at least one of copper and copper oxide, copper/zinc oxide-containing catalysts obtained by the above-described method, which show a half width of from 0.4 to 1.1 of a peak having a peak top at a position at which a diffraction angle ($2\theta \pm 0.2°$) is 43.1°, exhibit a high degree of activity as a catalyst in producing propylene glycol by performing catalytic hydrogenation of glycerol. The reason for this is presumed to be, for example, that if the half width is less than 0.4, the contact efficiency of the glycerol with the catalyst is poor, whereas if the half width is greater than 1.1, reduction in the activity is caused due to destabilization of the catalyst.

When a catalyst having a half width of less than 0.4 or a catalyst having a half width of greater than 1.1 is used, the conversion of glycerol is lowered. Accordingly, a high conversion of glycerol can be achieved when a copper/zinc oxide-containing catalyst having a half width of from 0.4 to 1.1 is used for producing propylene glycol by performing catalytic hydrogenation of glycerol. As a result, propylene glycol can be obtained at high yield. The half width is preferably from 0.5 to 1.1.

Next, the method of producing the specific catalyst will be described.

The specific catalyst can be produced by a known process called a coprecipitation process, an impregnation process, or a kneading process, in which at least one metal compound including copper and at least one metal compound including zinc, and optionally at least one metal compound including a metal in the third component, are used as the raw materials. Among these, a coprecipitation process is preferable in view of favorable dispersibility of copper.

Examples of the metal compound containing copper include a nitrate, a sulfate, a carbonate, an acetate, a chloride, an oxide, a hydroxide, and the like, of copper. Examples of the metal compound including zinc include a nitrate, a sulfate, a carbonate, an acetate, a chloride, an oxide, a hydroxide, and the like, of zinc. In addition, examples of the metal compound including a metal contained in the third component (hereinafter sometimes referred to as a "third metal") include a nitrate, a sulfate, a carbonate, an acetate, a chloride, an oxide, a hydroxide, and the like, of a third metal, as well as silica, colloidal silica, sodium silicate, and the like.

In the production of the specific catalyst, the coprecipitation process is a process in which, for example, a coprecipitant containing copper and zinc is produced by dropping, in water, an aqueous solution or a dispersion containing a nitrate of copper, a nitrate of zinc, and optionally a nitrate of third metal, silica, colloidal silica or the like, at the same time with an aqueous solution including a base such as sodium carbonate, and then drying and calcining the coprecipitant. In this process, catalysts containing copper oxide/zinc oxide in various copper/zinc ratios or catalysts containing copper oxide/zinc oxide/third component in which the third component is present at different contents can be produced by, for example, changing the ratio of the amounts of the raw materials such as a nitrate of copper and a nitrate of zinc.

The coprecipitant obtained in this coprecipitation process is dried and subsequently calcined before being used in the main reaction. The drying is carried out at 100 to 120° C. for 3 to 10 hours. The calcination temperature is 300° C. or higher, but preferably from 400 to 500° C. for the calcination of the catalyst used in the present reaction.

The impregnation process is a process of obtaining a mixture, and drying and calcining the same in accordance with the following steps. Examples of the method of obtaining the mixture in the impregnation process include a method in which a mixture containing copper and zinc, a mixture containing copper and a third metal, or a mixture containing zinc and a third metal, which can be obtained by the coprecipitation process, is suspended in water or the like, an aqueous solution or a suspension containing a metal that constitutes the remaining component is added thereto, and then the solvent such as water is removed therefrom, whereby a mixture containing copper, zinc and a third metal is obtained.

The kneading process is a process of obtaining a mixture, and drying and calcining the same in accordance with the following steps. Examples of the method of obtaining the mixture in the kneading process include a method of mixing respective components that constitute the specific catalyst being in a state of a solid or suspended in a solvent, and a method of mixing a mixture containing copper and zinc, a mixture containing copper and a third metal, or a mixture containing zinc and a third metal, which can be obtained by the coprecipitation process or the like and is in a state of a solid or suspended in a solvent, with a metal compound containing a metal that constitutes the remaining component.

The same raw materials as that described in the coprecipitation process can be used also in the impregnation process and the kneading process. In addition, when the mixture obtained by the impregnation process or the kneading process is dried and calcined, the same process carried out in the coprecipitation process can be applied.

The method of preparing the specific catalyst having a half width of from 0.4 to 1.1 is not particularly limited, and it can be controlled by, for example, controlling the calcination temperature or the calcination time of the catalyst obtained by the coprecipitation process or the like. When the calcination temperature is low or the calcination time is short, a large half width is obtained, whereas when the calcination temperature is high or the calcination time is long, a small half width tends to be obtained. The preferable calcination temperature and calcination time vary depending on the composition of the catalyst or the method of preparing the catalyst, but for example, in the case that the catalyst is obtained by a coprecipitation process, the calcination temperature is preferably from 400° C. to 500° C. and the calcination time is preferably from 2.5 hours to 6 hours, and the calcination temperature is more preferably from 400° C. to 500° C. and the calcination time is more preferably from 2.5 hours to 4 hours.

Among the obtained catalysts containing zinc oxide and at least one of copper and copper oxide, the catalyst having a half width of from 0.4 to 1.1 as measured by the above-described process is used as the specific catalyst for reaction for producing propylene glycol by performing catalytic hydrogenation of glycerol.

Next, the step of obtaining propylene glycol by performing catalytic hydrogenation of glycerol in the presence of the specific catalyst will be described.

The specific catalyst may be used as it is for the reaction for producing propylene glycol by performing catalytic hydrogenation of glycerol, or may be activated by reducing the same with hydrogen before being used for the reaction. This reduction is typically carried out by bringing the catalyst into contact with a hydrogen gas at 180 to 230° C. The catalyst used in the present invention may be in the form of a powder, or may be a product shaped by a known method such as compression, tableting, extrusion, granulation, atomization, grinding, or a method of forming into spheres in oil (see, for example, Catalyst Lecture 5, Catalyst Design, Chapter 4, page 116, edited by the Catalysis Society of Japan, Kodansha, 1985).

The amount of the catalyst to be used is not particularly limited by the type of the reaction, but is preferably from 0.1 to 20% by weight, and more preferably from 1 to 10% by weight, with respect to 100% weight of glycerol.

In the method of producing propylene glycol of the present invention, propylene glycol is obtained by performing catalytic hydrogenation of glycerol, and the glycerol may be used either as it is or as a solution of water or an organic solvent. The amount of water or the organic solvent to be used is not particularly limited, but it is typically from 10 to 90% by weight with respect to 100% weight of glycerol. From the viewpoint of volume efficiency or reaction rate, the above amount is preferably from 20 to 70% by weight.

The reactor used for the production method of the present invention is not particularly limited, and examples thereof include a batch reactor such as an autoclave, and a continuous reactor such as a fixed-bed catalytic reactor, a fluidized-bed catalytic reactor or a moving-bed catalytic reactor. In view of industrial advantages, a continuous reactor is preferably used.

In the present invention, the method of charging the catalyst into the reactor is not particularly limited as long as the reaction is not impeded.

Typically, the reaction (catalytic hydrogenation) can be carried out at a reaction temperature in a range of from 150° C. to 250° C., preferably from 180° C. to 220° C., and more preferably from 180° C. to 210° C., either under continuous conditions or in a batch system. By setting the reaction temperature to be 250° C. or lower, increase in the amount of the side-product can be suppressed, and the selectivity of propylene glycol can be improved. Further, reduction in the activity of a solid catalyst can be suppressed and the life time of the catalyst can be extended. In addition, by setting the reaction temperature to be 150° C. or higher, the reaction rate can be increased and the production efficiency of propylene glycol can be increased.

Further, under continuous conditions or in a batch system, the reaction (catalytic hydrogenation) is generally carried out at a reaction pressure of from 2 MPa to 30 MPa, preferably from 2 MPa to 15 MPa, and more preferably from 3 MPa to 15 MPa. When the pressure is within this range, the reaction rate is sufficiently high and propylene glycol can be efficiently obtained.

During the reaction, for the purpose of controlling the reaction pressure or the like, the reaction can be carried out in the presence of an inert gas such as nitrogen or the like in the reaction system.

The reaction time in the batch system or the contact time of glycerol with the catalyst in the continuous reaction is not particularly limited, but the reaction time in the batch reaction is usually from 1 to 12 hours, and preferably from 2 to 10 hours. Further, the contact time of glycerol with the catalyst in the continuous reaction is usually from 0.01 to 10 hours, preferably from 0.05 to 5 hours, and more preferably from 0.05 to 2 hours. By setting the contact time not to be less than the lower limit as described above, the reaction rate of glycerol can be increased and the process of separation/recovery of the reaction product can be more efficient. In addition, by setting the contact time not to be more than the upper limit as described above, the production efficiency of propylene glycol can be increased.

Since the specific catalyst is used in the method of producing propylene glycol of the present invention, a high yield can be achieved, and propylene glycol can be produced efficiently in industrial production. Further, the facilities can be minimized and the purification load after the reaction can be reduced. Moreover, if the reaction (catalytic hydrogenation) is carried out in a liquid phase, propylene glycol can be produced from glycerol at high yield without vaporizing the glycerol. However, the catalytic hydrogenation of glycerol can be carried out by catalytic hydrogenation in which glycerol is vaporized. In addition, it is also possible to carry out a process of removing poison in catalysis from glycerol as a raw material, or other processes as appropriate, prior to carrying out the catalytic hydrogenation of glycerol.

EXAMPLES

Hereinbelow, the present invention will be described in more detail with reference to the Examples, but the present invention is not limited thereto. For the measurement of X-ray diffraction of the catalyst containing zinc oxide and at least one of copper and copper oxide, RINT-1500 (manufactured by Rigaku Corporation, radiation sources: Cu, K$\alpha$1) was used, and for the measurement of half width, "RINT 2000 series application software, Analysis of Crystallite Size and Lattice Strain" (manufactured by Rigaku Corporation) was used. The conversion of glycerol and the yield of propylene glycol were calculated by gas chromatography (gas chromatography device: GC-14A, manufactured by Shimadzu Corporation, column: HP-INNOWAX manufactured by Agilent Technologies, detector: FID).

<Preparation Example of Catalyst 1>
—Preparation of Copper Oxide/Zinc Oxide (50/50 (% by Weight)) Catalyst and Measurement of Half Width—
(a) Preparation of Catalyst A-1 (Copper Oxide/Zinc Oxide (50/50 (% by Weight)))

Copper nitrate trihydrate (22.8 g) and zinc nitrate hexahydrate (27.5 g) were dissolved in distilled water to obtain 300 ml of an aqueous solution (hereinafter abbreviated as "aqueous solution B"). Meanwhile, anhydrous sodium carbonate (25.7 g) was dissolved in distilled water to obtain 450 ml of an aqueous solution (hereinafter abbreviated as "aqueous solution C"). Then, the aqueous solution B and the aqueous solution C were respectively dropped into 150 ml of distilled water while vigorously stirring the same at a rate of 3 ml/min, and the obtained precipitates were collected by filtration and washed with 400 ml of distilled water four times. The obtained solid was dried at 110° C. for 3 hours and calcined at a temperature of 400° C. for 2.5 hours in air. From the elemental analysis values of the obtained solid, it was found that the solid was copper oxide/zinc oxide (50/50 (% by weight)) (hereinafter abbreviated as "catalyst A-1").

(b) Reduction of Catalyst A-1
The catalyst A-1 above (0.75 g) was weighed and charged into a quartz glass tube having an inner diameter of 14 mm and an outer diameter of 20 mm. Under a nitrogen gas stream, the temperature was elevated such that the inside temperature was 185° C. and the outside temperature was 188° C. A gas mixture of nitrogen gas (15 ml/min) and hydrogen gas (4.5 ml/min) was allowed to flow for 0.5 hours. Thereafter, a gas mixture of nitrogen gas (15 ml/min) and hydrogen gas (9 ml/min) was further allowed to flow for 1.5 hours, whereby a copper/zinc oxide catalyst (hereinafter simply referred to as catalyst B-1) was obtained. During the reduction, the inside temperature was from 185 to 195° C. and the outside temperature was from 188 to 195° C. The catalyst B-1 was recovered in a nitrogen box.

(c) Preparation of Sample for X-Ray Diffraction Measurement

In a nitrogen box, 0.35 g of the catalyst B-1 above was weighed and placed in an agate mortar. 0.5 ml of acetone were added to wet the catalyst, and then 3.0 ml of CLEAR LACQUER (trade name, manufactured by Washin Paint Co., Ltd.) were added thereto. After stirring the mixture for 30 minutes, a viscous suspension was obtained. This suspension was applied on a glass cell for X-ray diffraction measurement, and dried overnight in the nitrogen box.

(d) X-Ray Diffraction Measurement
The obtained sample for X-ray diffraction measurement of the catalyst B-1 was taken out from the nitrogen atmosphere, and X-ray diffraction measurement was conducted in air. Thereafter, the half width of each peak was measured. The half width of a peak having a peak top at a diffraction angle 2θ=43.1° was 1.06.

—Reproducibility of Half Width—
The procedures described as (b) to (d) above were carried out for four samples obtained by using the catalyst A-1. Thereafter, the X-ray diffraction of the four samples was measured, and the half width of a peak having a peak top at a diffraction angle 2θ=43.1° was measured. The half widths of the samples were 1.03, 1.05, 1.08, and 1.06, respectively.

From the results as described above, it was found that the substantially same half width of a peak having a peak top at a position at which a diffraction angle 2θ=43.1 was observed when X-ray diffraction measurement was carried out for a copper/zinc oxide catalyst obtained by reducing a copper oxide/zinc oxide-containing catalyst.

<Preparation Example of Catalyst 2>
(a) Preparation of Catalyst A-23 (Copper Oxide/Zinc Oxide (70/30 (% by Weight))

Copper nitrate trihydrate (31.9 g) and zinc nitrate hexahydrate (16.5 g) were dissolved in distilled water to obtain 300 ml of an aqueous solution (hereinafter abbreviated as "aqueous solution B'"). Meanwhile, anhydrous sodium carbonate (25.8 g) was dissolved in distilled water to obtain 300 ml of an aqueous solution (hereinafter abbreviated as "aqueous solution C'"). Then, the aqueous solution B' and the aqueous solution C' were respectively dropped into 150 ml of distilled water while vigorously stirring the same at a rate of 3 ml/min, and the obtained precipitates were collected by filtration and washed with 300 ml of distilled water four times. The obtained solid was dried at 110° C. for 3 hours and calcined at a temperature of 300° C. for 3 hours in air, whereby a catalyst A-23 of copper oxide/zinc oxide (70/30 (% by weight)) was obtained.

<Preparation Example of Catalyst 3>
(a) Preparation of Catalysts A-2 to A-22, A-24 and A-25
Catalysts A-2 to A-22, A-24, and A-25 were obtained in the same manner as the catalyst A-1, except that the ratio of copper oxide and zinc oxide, the calcination temperature, and the calcination time were changed to the values as shown in Table 1 below.

Further, catalysts B-2 to 25 were prepared by carrying out the same operation as that carried out in the preparation of catalyst A-1 with respect to the catalysts A-2 to 25, and X-ray diffraction measurement was conducted. The results (the half width of a peak having a peak top at a position at which a diffraction angle 2θ is 43.1° in the X-ray diffraction pattern obtained by using CuKα as a radiation source is simply denoted as "half width" in Table 1, and the same also applies to Tables 2 to 5 described later) are shown in Table 1.

TABLE 1

| Catalyst name | Copper oxide/ zinc oxide (weight ratio) | Calcination conditions (temperature/time) | Half width | Note |
|---|---|---|---|---|
| A-1 | 50/50 | 400° C./2.5 hr | 1.06 | The invention |
| A-2 | 50/50 | 400° C./3 hr | 0.76 | The invention |
| A-3 | 50/50 | 400° C./3 hr | 0.72 | The invention |
| A-4 | 50/50 | 400° C./3 hr | 0.62 | The invention |
| A-5 | 50/50 | 400° C./4 hr | 0.56 | The invention |
| A-6 | 50/50 | 500° C./3 hr | 0.45 | The invention |
| A-7 | 60/40 | 400° C./3 hr | 1.05 | The invention |
| A-8 | 60/40 | 400° C./3.5 hr | 0.72 | The invention |
| A-9 | 60/40 | 500° C./3 hr | 0.47 | The invention |
| A-10 | 40/60 | 400° C./3 hr | 1.08 | The invention |
| A-11 | 40/60 | 400° C./3.5 hr | 0.78 | The invention |
| A-12 | 40/60 | 500° C./3 hr | 0.44 | The invention |
| A-13 | 70/30 | 400° C./3 hr | 0.55 | The invention |
| A-14 | 30/70 | 400° C./3 hr | 0.92 | The invention |
| A-15 | 30/70 | 500° C./3 hr | 0.66 | The invention |
| A-16 | 30/70 | 550° C./3 hr | 0.51 | The invention |
| A-17 | 50/50 | 300° C./3 hr | 1.51 | Comparative |
| A-18 | 50/50 | 600° C./3 hr | 0.32 | Comparative |
| A-19 | 60/40 | 300° C./3 hr | 1.65 | Comparative |
| A-20 | 60/40 | 550° C./3 hr | 0.37 | Comparative |
| A-21 | 40/60 | 300° C./3 hr | 1.34 | Comparative |
| A-22 | 40/60 | 550° C./3 hr | 0.36 | Comparative |
| A-23 | 70/30 | 300° C./3 hr | 1.12 | Comparative |
| A-24 | 70/30 | 500° C./3 hr | 0.34 | Comparative |
| A-25 | 30/70 | 300° C./3 hr | 1.95 | Comparative |

—Reduction Conditions for Catalyst A-1 and Half Width—

A reduced catalyst was prepared by reducing the catalyst A in the same manner as the catalyst B-1, except that the reduction conditions for the catalyst A-1 were changed to the temperature conditions as shown in Table 2 below. The half width of the reduced catalyst was measured. The results are shown in Table 2.

TABLE 2

| Catalyst name | Reduction conditions | | Half width |
|---|---|---|---|
| | Inside temperature (° C.) | Outside temperature (° C.) | |
| A-1 | 160 to 170 | 160 to 175 | 1.40 |
| | 215 to 225 | 220 to 230 | 0.83 |

Example 1

24 g of glycerol, 6 g of distilled water, and 1.2 g of catalyst A-1 were weighed and charged in a 100-ml autoclave made of SUS316 equipped with an electromagnetic rotation-induced stirring device.

The inside of the autoclave was substituted with nitrogen (10 MPa×5 times), and then substituted with hydrogen (10 MPa×5 times), and finally filled with hydrogen until the inside pressure was 10 MPa at room temperature, and the autoclave was sealed. While the reaction solution containing the catalyst in the autoclave was stirred at a stirring rate of 450 rpm, the autoclave was heated to 200° C. to cause catalytic hydrogenation reaction. 12 hours later, the heating was stopped and the autoclave was naturally cooled. When the inside temperature of the autoclave was decreased to 30° C. or lower, the inside was substituted with nitrogen and the autoclave was opened. The catalyst was removed from the content by filtration, and the obtained reaction solution was analyzed by means of gas chromatography. The conversion of glycerol was 86.4% and the yield of propylene glycol was 80.4%.

Examples 2 to 16 and Comparative Examples 1 to 9

Propylene glycol was obtained by performing catalytic reduction of glycerol (catalytic hydrogenation reaction) by the same method as in Example 1, except that catalysts A-2 to 25 were used instead of catalyst A-1 in Example 1. The conversion of glycerol and the yield of propylene glycol are shown in Table 3.

TABLE 3

| | Catalyst name | Half width | Conversion of glycerol (%) | Yield of propylene glycol (%) |
|---|---|---|---|---|
| Example 1 | A-1 | 1.06 | 86.4 | 80.4 |
| Example 2 | A-2 | 0.76 | 91.6 | 86.6 |
| Example 3 | A-3 | 0.72 | 91.4 | 85.8 |
| Example 4 | A-4 | 0.62 | 91.2 | 86.1 |
| Example 5 | A-5 | 0.56 | 90.3 | 84.9 |
| Example 6 | A-6 | 0.45 | 84.1 | 80.1 |
| Example 7 | A-7 | 1.05 | 81.3 | 75.7 |
| Example 8 | A-8 | 0.72 | 87.2 | 82.8 |
| Example 9 | A-9 | 0.47 | 81.3 | 76 |
| Example 10 | A-10 | 1.08 | 81.8 | 77.5 |
| Example 11 | A-11 | 0.78 | 86.8 | 81.6 |
| Example 12 | A-12 | 0.44 | 80.2 | 74.6 |
| Example 13 | A-13 | 0.55 | 84.3 | 80.7 |
| Example 14 | A-14 | 0.92 | 76.3 | 72.7 |
| Example 15 | A-15 | 0.66 | 74.2 | 71.6 |
| Example 16 | A-16 | 0.51 | 65.3 | 60.7 |
| Comparative Example 1 | A-17 | 1.51 | 64.1 | 59 |
| Comparative Example 2 | A-18 | 0.32 | 64.8 | 60.3 |
| Comparative Example 3 | A-19 | 1.65 | 58.3 | 54.2 |
| Comparative Example 4 | A-20 | 0.37 | 72.3 | 67.2 |
| Comparative Example 5 | A-21 | 1.34 | 70.6 | 66.4 |
| Comparative Example 6 | A-22 | 0.36 | 71.8 | 66.1 |
| Comparative Example 7 | A-23 | 1.12 | 53.6 | 49.1 |
| Comparative Example 8 | A-24 | 0.34 | 72.8 | 66.6 |
| Comparative Example 9 | A-25 | 1.95 | 49.8 | 46.6 |

From Tables 1 and 3, it was found that the copper oxide/zinc oxide-containing catalyst having a half width of from 0.4 to 1.1 exhibited a high conversion of glycerol. It was also found that the catalyst in which the ratio of copper oxide/zinc oxide was from 40/60 (weight ratio) to 60/40 (weight ratio) exhibited an even higher conversion of glycerol.

Example 17

A fixed-bed continuous reaction device made of Hastelloy C276 having a reaction tube with an inner diameter of 9 mm was filled with catalyst A-1 (5.0 g (5.9 ml)) described in Table 1, and hydrogen was allowed to flow at a rate of 20 ml/min at from 170° C. to 180° C. for 2 hours. Thereafter, a portion filled with the catalyst was heated to 195° C. To this catalyst-filled portion, a 80% by weight aqueous glycerol solution and hydrogen were supplied at 3 g/hr and 50 ml/hr (hydrogen/glycerol supply molar ratio=5.2/1), respectively, and this was allowed to initiate reaction. During the reaction, the pressure inside the reaction tube was kept at 3 MPa. Five hours later, a solution flowing out of the reaction tube was collected over 1 hour, and the collected solution was analyzed. The conversion of glycerol was 76.7%, the yield of propylene glycol was 71.3%, and the yield of propylene glycol per volume of the catalyst-filled portion per hour was 0.36 kg/L/hr.

Example 18

Catalytic hydrogenation of glycerol was carried out in the same manner as in Example 17, except that the catalyst A-2 was used instead of the catalyst A-1. As a result, the conversion of glycerol was 78.2%, the yield of propylene glycol was 72.8%, and the yield of propylene glycol per volume of the catalyst-filled portion per hour was 0.37 kg/L/hr.

Comparative Example 10

Catalytic hydrogenation of glycerol was carried out in the same manner as in Example 17, except that the catalyst A-18 was used instead of the catalyst A-1. As a result, the conversion of glycerol was 56.4%, the yield of propylene glycol was 52.4%, and the yield of propylene glycol per volume of the catalyst-filled portion per hour was 0.26 kg/L/hr.

Comparative Example 11

Catalytic hydrogenation of glycerol was carried out in the same manner as in Example 17, except that the catalyst A-17 was used instead of the catalyst A-1. As a result, the conversion of glycerol was 46.8%, the yield of propylene glycol was 43.4%, and the yield of propylene glycol per volume of the catalyst-filled portion per hour was 0.21 kg/L/hr.

<Preparation Example of Catalyst 4>

(a) Preparation of Catalyst A-26 (Copper Oxide/Zinc Oxide/Silica (50/40/10 (% by Weight)))

Copper nitrate trihydrate (38.0 g), zinc nitrate hexahydrate (36.6 g), and 12.5 g of colloidal silica (manufactured by Nissan Chemical Industries, Ltd., SNOWTEX O, silica concentration: 20% by weight) were added to distilled water and stirred, thereby preparing 500 ml of a dispersion (hereinafter abbreviated as "dispersion D"). Meanwhile, an aqueous solution of anhydrous sodium carbonate (32.7 g) was dissolved in distilled water, thereby preparing 500 ml of an aqueous solution (hereinafter abbreviated as "aqueous solution E"). Then, the dispersion D and the aqueous solution E were dropped at the same time into 300 ml of distilled water at a rate of 3 ml/min while vigorously stirring, thereby causing a reaction. The obtained precipitate was collected by filtration and washed with distilled water. The obtained solid was dried at 110° C. for 3 hours and calcined at a temperature of 400° C. for 3 hours in air. From the elemental analysis values of the obtained solid, it was found that the solid was copper oxide/zinc oxide/silica=50/40/10 (% by weight) (hereinafter abbreviated as "catalyst A-26").

(b) Reduction of Catalyst A-26

The catalyst A-26 above (0.75 g) was weighed and charged in a quartz glass tube having an inner diameter of 14 mm and an outer diameter of 20 mm. While allowing a nitrogen gas to flow, the temperature was elevated so that the inside temperature was 210° C. and the outside temperature was 215° C. A gas mixture of nitrogen gas (15 ml/min) and hydrogen gas (4.5 ml/min) was allowed to flow for 0.5 hours. Thereafter, a gas mixture of nitrogen gas (15 ml/min) and hydrogen gas (9 ml/min) was further allowed to flow for 1.5 hours, thereby obtaining a copper/zinc oxide/silica catalyst (hereinafter simply referred to as catalyst B-26). During performing the reduction, the inside temperature was from 210 to 220° C. and the outside temperature was from 215 to 225° C. The catalyst B-26 was recovered in a nitrogen box.

(c) Preparation of Sample for X-Ray Diffraction Measurement

In a nitrogen box, 0.35 g of the catalyst B-26 above was weighed and placed in an agate mortar. 0.5 ml of acetone were added to wet the catalyst, and then 3.0 ml of CLEAR LACQUER (trade name, manufactured by Washin Paint Co., Ltd.) was further added thereto. After stirring the mixture for 30 minutes, a viscous suspension was obtained. The suspension was applied on a glass cell for X-ray diffraction measurement, and dried overnight in the nitrogen box.

(d) X-Ray Diffraction Measurement

The obtained sample for X-ray diffraction measurement of the catalyst B-26 was taken out from the nitrogen atmosphere, and X-ray diffraction measurement was conducted in air. Thereafter, the half width of each peak was measured. The half width of a peak having a peak top at a diffraction angle 2θ=43.1 was 0.95.

<Preparation Example of Catalyst 5>

(a) Preparation of Catalysts A-27 to A-30

Catalysts A-27 to A-30 shown in Table 4 were obtained in the same manner as the preparation of the catalyst A-26, except that the ratio of copper oxide, zinc oxide, and colloidal silica, the calcination temperature, and the calcination time were changed to the values as shown in Table 4 below.

For the obtained catalysts A-27 to A-30, a reduction treatment was carried out in the same manner as the catalyst A-26, and the half width of each catalyst was measured. The results are shown in Table 4.

TABLE 4

| Catalyst name | Catalyst composition (weight ratio) | Calcination condition (temperature/time) | Reduction condition (inside temperature/time) | Half width | Note |
|---|---|---|---|---|---|
| A-26 | CuO/ZnO/SiO$_2$ (50/40/10) | 400° C./3 hr | 210 to 220° C./2 hr | 0.95 | The invention |
| A-27 | CuO/ZnO/SiO$_2$ (50/40/10) | 500° C./3 hr | 210 to 220° C./2 hr | 0.73 | The invention |
| A-28 | CuO/ZnO/SiO$_2$ (50/35/15) | 400° C./3 hr | 210 to 220° C./2 hr | 0.88 | The invention |
| A-29 | CuO/ZnO/SiO$_2$ (60/30/10) | 400° C./3 hr | 210 to 220° C./2 hr | 0.86 | The invention |
| A-30 | CuO/ZnO/SiO$_2$ | 400° C./3 hr | 210 to 220° C./2 hr | 1.04 | The |

TABLE 4-continued

| Catalyst name | Catalyst composition (weight ratio) | Calcination condition (temperature/time) | Reduction condition (inside temperature/time) | Half width | Note |
|---|---|---|---|---|---|
| A-31 | CuO/ZnO/Fe$_2$O$_3$ (45/45/10) | 400° C./3 hr | 210 to 220° C./2 hr | 0.76 | The invention |
| A-32 | CuO/ZnO/MgO (45/45/10) | 400° C./3 hr | 210 to 220° C./2 hr | 1.06 | The invention |
| A-33 | CuO/ZnO/SiO$_2$ (45/45/10) | 400° C./3 hr | 210 to 220° C./2 hr | 0.83 | The invention |

<Preparative Example 6 of Catalyst>

(a) Preparation of Catalyst A-31 (Copper Oxide/Zinc Oxide/Iron Oxide (45/45/10 (% by Weight)))

Copper nitrate trihydrate (13.7 g), zinc nitrate hexahydrate (16.5 g), and ferric nitrate nonahydrate (5.1 g) were dissolved in distilled water to obtain 300 ml of an aqueous solution (hereinafter abbreviated as "aqueous solution F"). Meanwhile, anhydrous sodium carbonate (25.8 g) was dissolved in distilled water to obtain 300 ml of an aqueous solution (hereinafter abbreviated as "aqueous solution G"). Then, the aqueous solution F and the aqueous solution G were each dropped into 150 ml of distilled water at a rate of 3 ml/min, while vigorously stirring, and the obtained precipitates were collected by filtration and washed with 300 ml of distilled water four times. The obtained solid was dried at 110° C. for 3 hours, and calcined at a temperature of 400° C. for 3 hours in air. From the elemental analysis value of the obtained solid, it was found that the solid was copper oxide/zinc oxide/iron oxide (45/45/10 (% by weight)) (hereinafter abbreviated as "catalyst A-31").

Catalyst B-31 was prepared from the catalyst A-31 by performing the same procedure as that carried out for the catalyst A-26, and X-ray diffraction measurement was carried out. As a result, the half width was 0.76.

<Preparative Example of Catalyst 7>

(a) Preparation of Catalyst A-32 (Copper Oxide/Zinc Oxide/Magnesium Oxide (45/45/10 (% by Weight)))

A catalyst of copper oxide/zinc oxide/magnesium oxide (45/45/10 (% by weight)) (hereinafter abbreviated as "catalyst A-32") was prepared from copper nitrate trihydrate (13.7 g), zinc nitrate hexahydrate (16.5 g), magnesium nitrate hexahydrate (6.4 g), and anhydrous sodium carbonate (18.8 g) as raw materials, by performing the same procedure as that carried out for the catalyst A-31.

Catalyst B-32 was prepared from the obtained catalyst A-32 by performing the same procedure as that carried out for the catalyst A-26, and X-ray diffraction measurement was carried out. As a result, the half width was 1.06.

<Preparation Example of Catalyst 8>

(a) Preparation of Catalyst A-33 (Copper Oxide/Zinc Oxide/Silica (45/45/10 (% by Weight)))

Copper nitrate trihydrate (15.2 g) and zinc nitrate hexahydrate (18.3 g) were dissolved in distilled water to obtain 300 ml of an aqueous solution (hereinafter abbreviated as "aqueous solution H"). Meanwhile, anhydrous sodium carbonate (17.1 g) was dissolved in distilled water to obtain 300 ml of an aqueous solution (hereinafter abbreviated as "aqueous solution J"). Then, the aqueous solution H and the aqueous solution J were dropped into 150 ml of distilled water at a rate of 3 ml/min, respectively. The obtained precipitates were collected by filtration and washed with 300 ml of distilled water four times. The obtained solid was dried at 110° C. for 3 hours.

To this solid, colloidal silica (2.8 g, trade name, LUDOX AS-40 (manufactured by Sigma-Aldrich Corporation), xanthan gum (1.0 g), and distilled water (10.5 g) were added, and thoroughly mixed. The mixture was extruded through a nozzle having a diameter of 3 mm, dried at 110° C. for 3 hours, and calcined at 400° C. for 3 hours in air. From the elemental analysis values of the obtained solid, it was found that the solid was copper oxide/zinc oxide/silica (45/45/10 (% by weight)) (hereinafter abbreviated as "catalyst A-33").

The catalyst A-33 was pulverized, subjected to measurement of a half width, and used for catalytic hydrogenation.

Catalyst B-33 was prepared from the catalyst A-33 by performing the same procedure as that carried out for the catalyst A-26, and subjected to X-ray diffraction measurement. As a result, the half width was 0.83.

Example 19

A fixed-bed continuous reaction device made of Hastelloy C276 having a reaction tube with an inner diameter of 9 mm was filled with the catalyst A-26 (5.0 g (5.9 ml)) shown in Table 4, and hydrogen was allowed to flow at a rate of 20 ml/min at an inside temperature of from 210° C. to 225° C. for 2 hours. Thereafter, the catalyst-filled portion was heated to 195° C. To this catalyst-filled portion, an 80% by weight aqueous glycerol solution and hydrogen were supplied at 3 g/hr and 50 ml/hr (hydrogen/glycerol supply molar ratio=5.2/1), respectively, and this was allowed to initiate reaction. During the reaction, the inside pressure of the reaction tube was kept at 3 MPa. Five hours later, a solution flowing out of the reaction tube was collected over 1 hour, and the collected solution was analyzed. The conversion of glycerol was 97.4%, the yield of propylene glycol was 93.2%, and the yield of propylene glycol per volume of the catalyst-filled portion per hour was 0.47 kg/L/hr.

Examples 20 to 26

Glycerol was subjected to catalytic hydrogenation with hydrogen in the same manner as in Example 19, except that catalysts A-27 to A-33 shown in Table 4 were used instead of the catalyst A-26 in Example 19. The results are shown in Table 5.

Example 27

A fixed-bed continuous reaction device made of Hastelloy C276 having a reaction tube with an inner diameter of 9 mm was filled with the catalyst A-26 (5.0 g (5.9 ml)) shown in Table 4, and hydrogen was allowed to flow at a rate of 20 ml/min at an inside temperature of from 210° C. to 225° C. for 2 hours. Thereafter, the catalyst-filled portion was heated to 220° C. To this catalyst-filled portion, an 80% by weight aqueous glycerol solution and hydrogen were supplied at 3 g/hr and 50 ml/hr (hydrogen/glycerol feeding molar ratio=5.2/1), respectively, thereby initiating the reaction. During the reaction, the inside pressure of the reaction tube was kept at 3 MPa. Five hours later, a solution flowing out of the reaction tube was collected over 1 hour, and the collected solution was analyzed. The conversion of glycerol was 99.8%, the yield of propylene glycol was 90.6%, and the yield of propylene glycol per volume of the catalyst-filled portion per hour was 0.45 kg/L/hr.

Example 28

A fixed-bed continuous reaction device made of Hastelloy C276 having a reaction tube with an inner diameter of 9 mm was filled with the catalyst A-26 (5.0 g (5.9 ml)) shown in Table 4, and hydrogen was allowed to flow at a rate of 20 ml/min at a temperature of from 210° C. to 225° C. for 2 hours. Thereafter, the catalyst-filled portion was heated to 180° C. To this catalyst-filled portion, an 80% by weight aqueous glycerol solution and hydrogen were supplied at 3 g/hr and 50 ml/hr (hydrogen/glycerol supply molar ratio=5.2/1), respectively, and this was allowed to initiate reaction. During the reaction, the inside pressure of the reaction tube was kept at 5 MPa. Five hours later, a solution flowing out of the reaction tube was collected over 1 hour, and the collected solution was analyzed. The conversion of glycerol was 83.6%, the yield of propylene glycol was 81.5%, and the yield of propylene glycol per volume of the catalyst-filled portion per hour was 0.41 kg/L/hr.

TABLE 5

| | Catalyst name | Half width | Reaction temperature (° C.) | Conversion of glycerol (%) | Yield of propylene glycol (%) |
|---|---|---|---|---|---|
| Example 19 | A-26 | 0.95 | 195 | 97.4 | 93.2 |
| Example 20 | A-27 | 0.73 | 195 | 92.1 | 88.1 |
| Example 21 | A-28 | 0.88 | 195 | 83.9 | 82.1 |
| Example 22 | A-29 | 0.86 | 195 | 85.9 | 79.1 |
| Example 23 | A-30 | 1.04 | 195 | 99.3 | 95.0 |
| Example 24 | A-31 | 0.76 | 195 | 91.9 | 88.6 |
| Example 25 | A-32 | 1.06 | 195 | 86.0 | 82.5 |
| Example 26 | A-33 | 0.83 | 195 | 99.5 | 95.2 |
| Example 27 | A-26 | 0.95 | 220 | 99.8 | 90.6 |
| Example 28 | A-26 | 0.95 | 180 | 83.6 | 81.5 |

From the results above, it was found that the conversion of glycerol and the yield of propylene glycol of a copper oxide/zinc oxide catalyst-containing showing a half width of from 0.4 to 1.1 of a peak having a peak top at a diffraction angle 2θ=43.1° are high, and as a result, the yield of propylene glycol per unit volume and unit time of the catalyst-filled layer (space time yield) is high.

The invention claimed is:

1. A method of producing propylene glycol, the method comprising:
   obtaining propylene glycol by performing catalytic hydrogenation of glycerol in the presence of a catalyst,
   the catalyst comprising a first component containing at least one of copper and copper oxide and a second component containing zinc oxide, and
   the catalyst, after being reduced at 180° C. to 230° C. in the presence of hydrogen, showing a half width of from 0.4 to 1.1 of a peak having a peak top at a position at which a diffraction angle (2θ±0.2°) is 43.1° in an X-ray diffraction pattern obtained using CuKα as a radiation source,
   wherein the catalyst has been subjected to a calcination treatment at a calcination temperature of from 400° C. to 500° C. for a calcination time of from 2.5 hours to 6 hours.

2. The method of producing propylene glycol according to claim 1, wherein a weight ratio of the first component to the second component ((total weight of copper and copper oxide)/(weight of zinc oxide)) in the catalyst is in a range of from 30/70 to 70/30.

3. The method of producing propylene glycol according to claim 2, wherein a weight ratio of the first component to the second component ((total weight of copper and copper oxide)/(weight of zinc oxide)) in the catalyst is in a range of from 40/60 to 60/40.

4. The method of producing propylene glycol according to claim 1, the catalyst further comprising a third component other than copper, copper oxide and zinc oxide.

5. The method of producing propylene glycol according to claim 2, the catalyst further comprising a third component other than copper, copper oxide and zinc oxide.

6. The method of producing propylene glycol according to claim 3, the catalyst further comprising a third component other than copper, copper oxide and zinc oxide.

7. The method of producing propylene glycol according to claim 4, wherein a content of the third component in the catalyst is 25% by weight or less.

8. The method of producing propylene glycol according to claim 5, wherein a content of the third component in the catalyst is 25% by weight or less.

9. The method of producing propylene glycol according to claim 6, wherein a content of the third component in the catalyst is 25% by weight or less.

10. The method of producing propylene glycol according to claim 4, wherein the third component is at least one selected from silica, iron oxide or magnesium oxide.

11. The method of producing propylene glycol according to claim 5, wherein the third component is at least one selected from silica, iron oxide or magnesium oxide.

12. The method of producing propylene glycol according to claim 6, wherein the third component is at least one selected from silica, iron oxide or magnesium oxide.

13. The method of producing propylene glycol according to claim 7, wherein the third component is at least one selected from silica, iron oxide or magnesium oxide.

14. The method of producing propylene glycol according to claim 8, wherein the third component is at least one selected from silica, iron oxide or magnesium oxide.

15. The method of producing propylene glycol according to claim 9, wherein the third component is at least one selected from silica, iron oxide or magnesium oxide.

16. The method of producing propylene glycol according to claim 1, wherein the catalytic hydrogenation of glycerol is carried out at a reaction pressure of from 2 to 30 MPa and a reaction temperature of from 150 to 250° C.

17. The method of producing propylene glycol according to claim 16, wherein the catalytic hydrogenation of glycerol is carried out at a reaction pressure of from 2 to 30 MPa and a reaction temperature of from 180 to 220° C.

* * * * *